US009322720B2

(12) United States Patent
Wernsman et al.

(10) Patent No.: US 9,322,720 B2
(45) Date of Patent: Apr. 26, 2016

(54) USE OF ALUMINUM NITRIDE TO OBTAIN TEMPERATURE MEASUREMENTS IN A HIGH TEMPERATURE AND HIGH RADIATION ENVIRONMENT

(71) Applicant: United States Department of Energy, Washington, DC (US)

(72) Inventors: Bernard R. Wernsman, Jefferson Hills, PA (US); Raymond J. Blasi, North Huntingdon, PA (US); Bernhard R. Tittman, State College, PA (US); David A. Parks, Tulsa, OK (US)

(73) Assignee: U.S. Department of Energy, Washington, DC (US)

( * ) Notice: Subject to any disclaimer, the term of this patent is extended or adjusted under 35 U.S.C. 154(b) by 283 days.

(21) Appl. No.: 14/186,244

(22) Filed: Feb. 21, 2014

(65) Prior Publication Data

US 2016/0018270 A1 Jan. 21, 2016

Related U.S. Application Data

(60) Provisional application No. 61/768,816, filed on Feb. 25, 2013.

(51) Int. Cl.
*G01K 11/22* (2006.01)
*G01N 29/24* (2006.01)

(52) U.S. Cl.
CPC .............. *G01K 11/22* (2013.01); *G01N 29/245* (2013.01)

(58) Field of Classification Search
CPC ....... G01K 11/22; G01K 11/02; G01K 9/122; H01L 41/053; H01L 41/067; H01L 41/29; G01N 29/24; G01N 29/326; G01N 29/348; G01N 29/225; G01N 29/245; G01N 29/223
USPC ............ 73/644, 649, 579, 632; 310/315, 334, 310/335, 336, 346; 367/99
See application file for complete search history.

(56) References Cited

U.S. PATENT DOCUMENTS

| | | | | | |
|---|---|---|---|---|---|
| 3,781,576 | A | * | 12/1973 | Runde | G10K 11/004 310/336 |
| 4,126,514 | A | * | 11/1978 | Wonn | G21C 17/07 376/252 |
| 4,551,647 | A | * | 11/1985 | Day | B06B 1/0651 29/25.35 |
| 4,622,202 | A | * | 11/1986 | Yamada | G21C 17/032 374/117 |
| 4,746,831 | A | * | 5/1988 | Ichino | G01F 1/662 310/327 |
| 4,825,117 | A | * | 4/1989 | Thomas, III | B06B 1/067 310/344 |
| 5,303,591 | A | * | 4/1994 | Dykes | B06B 1/0215 73/620 |
| 5,325,012 | A | * | 6/1994 | Sato | H01L 41/313 228/121 |
| 5,332,943 | A | * | 7/1994 | Bhardwaj | B06B 1/0681 310/326 |
| 5,376,860 | A | * | 12/1994 | Sato | H01L 41/1132 310/338 |
| 8,166,824 | B2 | * | 5/2012 | Sugiura | G01S 7/52 73/1.82 |
| 2007/0157728 | A1 | * | 7/2007 | Endou | B06B 1/0261 73/579 |
| 2012/0155221 | A1 | * | 6/2012 | Bagshaw | G01S 15/96 367/137 |

* cited by examiner

*Primary Examiner* — Helen Kwok
(74) *Attorney, Agent, or Firm* — Robert T. Burns; John T. Lucas

(57) ABSTRACT

An aluminum nitride piezoelectric ultrasonic transducer successfully operates at temperatures of up to 1000° C. and fast (>1 MeV) neutron fluencies of more than $10^{18}$ n/cm². The transducer comprises a transparent, nitrogen rich aluminum nitride (AlN) crystal wafer that is coupled to an aluminum cylinder for pulse-echo measurements. The transducer has the capability to measure in situ gamma heating within the core of a nuclear reactor.

19 Claims, 4 Drawing Sheets

USE OF ALUMINUM NITRIDE TO OBTAIN TEMPERATURE MEASUREMENTS IN A HIGH TEMPERATURE AND HIGH RADIATION ENVIRONMENT

STATEMENT REGARDING FEDERALLY SPONSORED RESEARCH AND DEVELOPMENT

This invention was made with U.S. Government support under Contract No. DE-NR0000031 awarded by the United States Department of Energy. The U.S. Government has certain rights in the invention.

TECHNOLOGICAL FIELD

The present subject matter relates to the use of aluminum nitride to obtain temperature measurements in a high-temperature and high-radiation environment. In particular, the present subject matter relates to the use of aluminum nitride to obtain temperature measurements in the high-temperature and high-radiation environment of a nuclear reactor.

DESCRIPTION OF RELATED ART

In-core temperature measurement is critical for the safe operation of nuclear reactors. Currently, there is no known piezoelectric material that can operate successfully in the high-temperature and high-radiation environment of a nuclear reactor. A material is piezoelectric when it can convert an electrical signal (e.g., field) to a mechanical motion (e.g., strain) and vice versa. There are two subsets of this material type: pyroelectric and ferroelectric. A pyroelectric piezoelectric material does not have a Curie temperature, while a ferroelectric piezoelectric material does. To produce sound in a material, the material needs to be piezoelectric. It is believed that piezoelectric materials begin to degrade at neutron fluencies of approximately $10^{17}$ n/cm$^2$ since they have not been tested for fluencies greater than $10^{15}$ n/cm$^2$ and typical solid-state devices begin to fail at this value. As a result, the use of ultrasonic measurement, inspection, and monitoring technologies is limited under these conditions. Accordingly, there is a need for an ultrasonic sensor that can operate successfully in both the high-temperature and high-radiation environment of a nuclear reactor.

BRIEF SUMMARY

The present subject matter proposes a transparent, nitrogen rich aluminum nitride (AlN) piezoelectric ultrasonic transducer (or sensor) that can successfully operate at temperatures of up to 1000° C. and fast (>1 MeV) neutron fluencies of more than $10^{18}$ n/cm$^2$. The transducer comprises an aluminum nitride crystal wafer, which is coupled to an aluminum cylinder for pulse-echo measurements. Aluminum nitride is a pyroelectric piezoelectric material, has the wurtzite structure, and cannot be depoled, making it an ideal candidate for this application. The transducer is placed in an aluminum capsule (transducer housing) and attached to cabling.

The transducer is capable of measuring in situ gamma heating within the reactor core, since the ultrasonic capability of AlN can survive temperatures of up to 1000° C. and fast (>1 MeV) neutron fluencies of up to $2 \times 10^{18}$ n/cm$^2$. By using the piezoelectric material (AlN) and aluminum cylinder assembly, the temperature of the cylinder inside a reactor operating at 1 MW$_t$ (including but not limited to a pool-type reactor) can be successfully measured via an ultrasonic time-of-flight method.

BRIEF DESCRIPTION OF THE DRAWINGS

The accompanying drawings illustrate exemplary non-limiting embodiments of the present subject matter and together with the descriptions below.

DETAILED DESCRIPTION

Reference will now be made to non-limiting illustrative embodiments of the present subject matter, examples of which are illustrated in the accompanying drawings.

Figure 1:
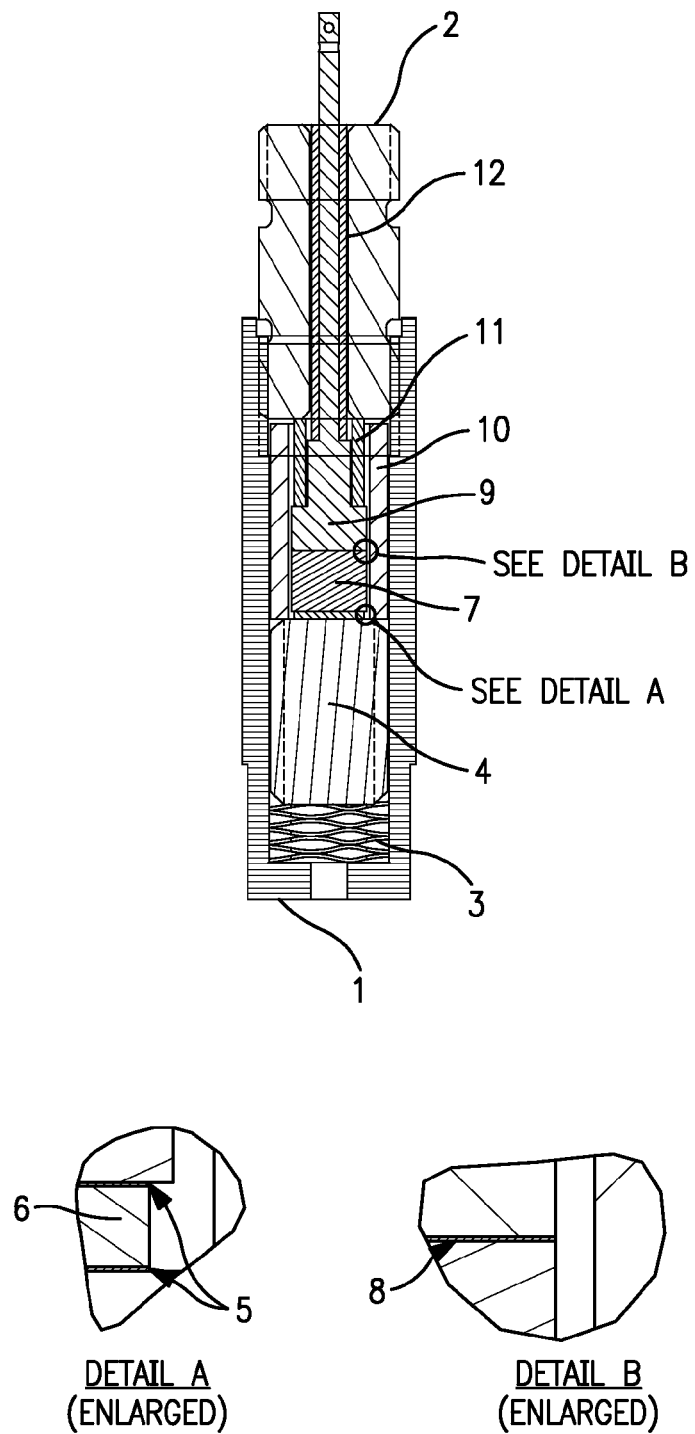
FIG. 1 shows a schematic view of a temperature sensor according to one embodiment of the subject matter.

FIG. 1 illustrates a temperature sensor (or transducer) assembly according to one embodiment of the present subject matter. The temperature sensor assembly comprises a transducer housing (1) and a cap (2) that encapsulates the sensor. The housing (1) and the cap (2) are electrically grounded and may be comprised of aluminum. Alternatively, they may be comprised of stainless steel or other material that is an electrical conductor. The temperature sensor assembly also comprises a wavespring (3) that maintains compression of the internal components of the sensor to achieve sufficient ultrasonic coupling and electrical connection among the internal components. Alternatively, a spring, pressurized bladder, or other mechanism for maintaining compression of the internal sensor components may be used in place of the wavespring (3). The temperature sensor assembly further comprises a sensor block (4). The thermal expansion of the sensor block (4) can be used to determine the temperature of a nuclear reactor core. The sensor block (4) is in the shape of a cylinder and may be made of aluminum. Alternatively, the block (4) may be made of other materials, such as stainless steel. The cylinder may be about 15 mm in diameter and about 65 mm in length. The wavespring (3) and the sensor block (4) are in electrical contact with the electrically grounded housing (1) and cap (2); so they are also electrically grounded. An adhesive (5) is used to attach a piezoelectric (6) and a carbon-carbon (C-C) backing (7) to the sensor block (4). The adhesive (5) is a high-temperature adhesive that is preferably electrically conductive. It can be insulating, however, as long as it is thin. The piezoelectric (6) is a 5.3 mm diameter single crystal z-cut of aluminum nitride. Aluminum nitride was selected because of its low damage cross section and remarkable damage annealing. Preferably, the wafer (6) is a transparent nitrogen rich AN. The wafer (6) is resonant at about 13 MHz. Preferably, the wafer (6) is resonant at 13.4 MHz. The C-C backing performs two functions: (i) to provide electrical conduction from an electrode (9) to the piezoelectric (6) and (ii) to diminish the ultrasonic ringing from the piezoelectric (6) through sound absorption. A foil (8) may be used to enhance the electrical conduction between the electrode (9) and the C-C backing (7). The foil may comprise any pliable material that can withstand reactor operating temperatures, such as aluminum, gold, or platinum. The electrode (9) is used for connecting an electrical cable to the sensor. Insulators (10)-(12) are used to electrically isolate the high-voltage electrode (9) from the grounded body (1) and cap (2). The insulators (10)-(12) may be made of alumina, for example. All aluminum components may be 6061 series aluminum, for example.

The operation of the temperature sensor assembly will now be discussed. A high voltage impulse is delivered to the piezoelectric (6) via the electrode (9) while the housing (1) and cap (2) are maintained at electrical ground. Due to the electric field across the piezoelectric (6), the piezoelectric (6) changes shape, creating a strain wave (ultrasonic pulse) in the sensor block (4). The ultrasonic pulse then travels to the opposite end of the sensor block (4) where it is reflected back (echoed), placing a stress upon the piezoelectric (6) and creating an electric field across it that is detected on the electrode (9) as an output electrical pulse. Since the sensor block (4) is allowed to thermally expand, the time it takes for an ultrasonic pulse to travel from one end of the block (4) to the other end and back—that is, the time between sending the electrical input pulse and receiving the echo (time-of-flight)—changes with temperature. This change in time-of-flight can be calibrated and used to measure the temperature in high-temperature and high-radiation environments.

Figure 2:
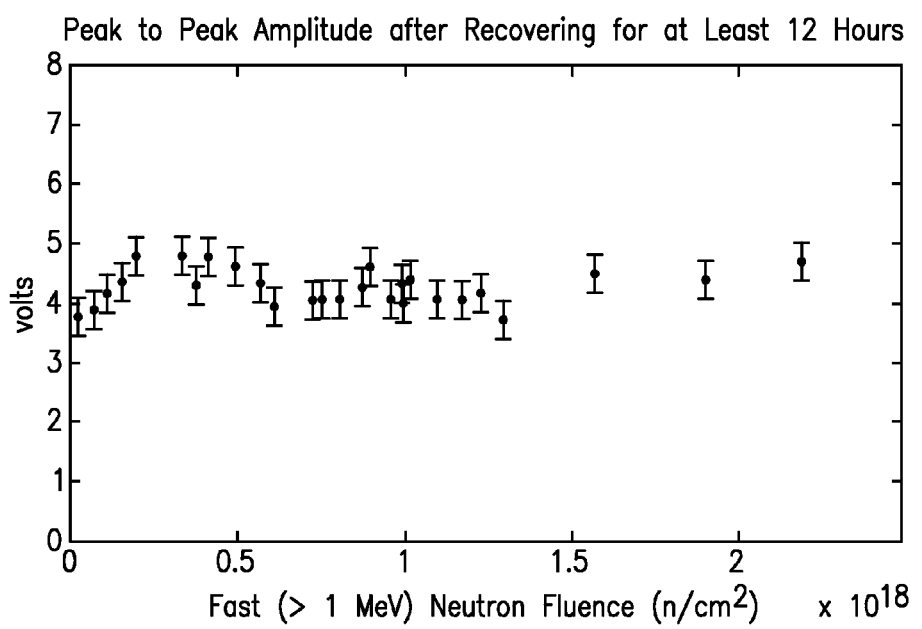
FIG. 2 illustrates an AlN pulse echo peak-to-peak amplitude ultrasonic response as a function of fast (>1 MeV) neutron fluence showing no degradation in response according to one embodiment of the subject matter.

FIG. 2. shows the measured echo peak-to-peak electrical output as a function of fast neutron fluence according to one embodiment of the subject matter. As shown, the echo amplitude did not degrade for a fast neutron fluence of at least $2\times10^{18}$ n/cm$^2$, indicating the survivability of the piezoelectric material in a neutron field.

Figure 3:
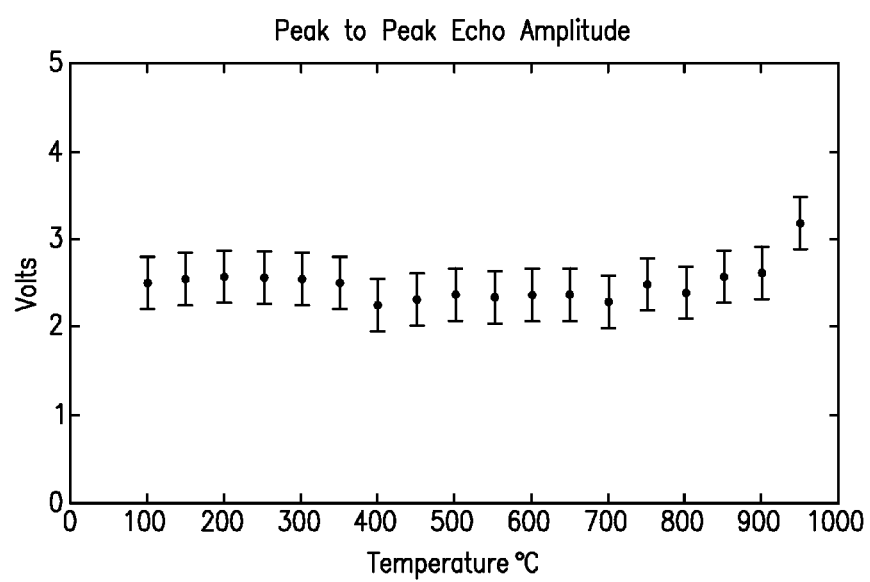
FIG. 3 illustrates a pulse echo peak-to-peak amplitude of aluminum nitride as a function of temperature showing no degradation according to one embodiment of the subject matter.

FIG. 3. shows the measured echo peak-to-peak amplitude electrical output as a function of temperature according to one embodiment of the subject matter. As shown, the echo amplitude did not degrade for a temperature of at least 950° C. indicating the thermal survivability of the piezoelectric material.

Figure 4:
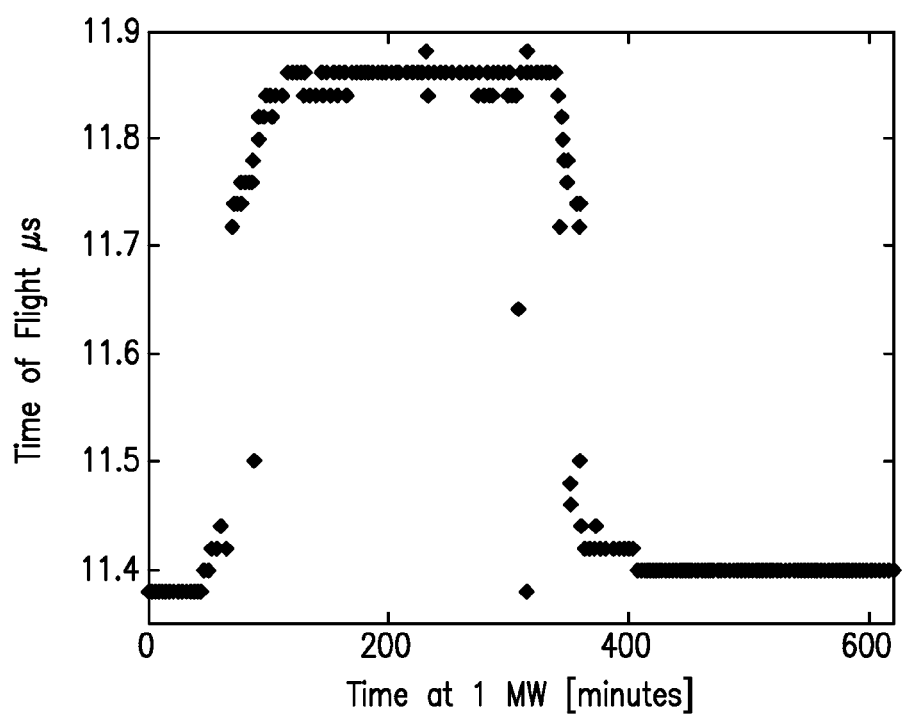
FIG. 4 illustrates an ultrasonic time of flight as effected by gamma heating according to one embodiment of the present subject matter.

FIG. 4. shows the measured time-of-flight before, during, and after the reactor was operated at 1 MW$_t$ according to one embodiment of the subject matter. As shown, the change in the time-of-flight was about 0.48 µs after the reactor was turned on. From a calibrated time-of-flight versus temperature relationship, this corresponded to a change in temperature of about 115° C., indicating that the sensor block reached a temperature of about 140° C. (room temperature plus 115° C.) during reactor operation.

It will be apparent to those skilled in the art that various modifications and variations can be made in the piezoelectric ultrasonic transducer of the present subject matter without departing from the spirit and scope of the subject matter. For example, the dimensions of the piezoelectric (6) may be chosen so that it fits within the temperature assembly, and the dimensions of the temperature assembly may be chosen so that it fits within a nuclear reactor. Further, the thickness of the piezoelectric (6) may be chosen according to the desired resonant frequency. Similarly, the dimensions of the sensor block (4) may be varied so long as the input pulse and echo can be distinguished from one another. It is intended that the present subject matter cover the modifications and variations of the subject matter, provided they come within the scope of the appended claims and their equivalents.

We claim:

1. A temperature sensing apparatus for testing a nuclear reactor, the temperature sensing apparatus comprising:
   an electrode;
   a piezoelectric wafer connected electrically to the electrode, the piezoelectric wafer withstanding neutron fluencies of 1018 n/cm$^2$ or more;
   a sensor block that thermally expands with a change in temperature in the nuclear reactor, the sensor block being connected to the piezoelectric wafer;
   a compression mechanism; and
   a transducer housing and a cap, both the transducer housing and the cap enclosing the piezoelectric wafer, the electrode, the sensor block, and the compression mechanism;
   wherein the transducer housing and the cap are electrically grounded, and the sensor block and the compression mechanism are connected electrically to the transducer housing and the cap; and
   wherein the apparatus is configured to measure within the nuclear reactor a time an ultrasonic pulse takes to travel from a first end of the sensor block to a second end of the sensor block and back to the first end of the sensor block.

2. The apparatus according to claim 1, wherein the apparatus is configured to measure via electrical pulses the time the ultrasonic pulse takes to travel from the first end of the sensor block to the second end of the sensor block and back to the first end of the sensor block.

3. The apparatus according to claim 1, wherein the piezoelectric wafer withstands temperatures of 1000° C. or more.

4. The apparatus according to claim 1, wherein the piezoelectric wafer comprises a pyroelectric piezoelectric material.

5. The apparatus according to claim 4, wherein the piezoelectric wafer comprises aluminum nitride.

6. The apparatus according to claim 4, wherein the piezoelectric wafer comprises a 5.3 mm diameter single crystal z-cut of aluminum nitride.

7. The apparatus according to claim 4, wherein the piezoelectric wafer comprises transparent nitrogen rich aluminum nitride.

8. The apparatus according to claim 1, wherein the piezoelectric wafer comprises a ferroelectric piezoelectric material.

9. The apparatus according to claim 4, further comprising an adhesive that attaches the piezoelectric wafer and a backing to the sensor block, the backing providing electrical conduction from the electrode to the piezoelectric wafer.

10. The apparatus according to claim 9, wherein the backing is a carbon-carbon backing.

11. The apparatus according to claim 4, wherein the sensor block is an aluminum cylinder, the aluminum cylinder being about 15 mm in diameter and about 65 mm in length.

12. The apparatus according to claim 1, further comprising insulators that electrically isolate the electrode from the transducer housing and the cap.

13. A method for testing a nuclear reactor comprising:
   (a) placing a temperature sensing apparatus within the nuclear reactor, the apparatus comprising an electrode; a piezoelectric wafer connected electrically to the electrode, the piezoelectric wafer withstanding neutron fluencies of 1018 n/cm$^2$ or more; and a sensor block that thermally expands with a change in temperature in the nuclear reactor, the sensor block being connected to the piezoelectric wafer;
   (b) applying an electrical input pulse to the piezoelectric wafer through the electrode;
   (c) creating at a first end of the sensor block an ultrasonic pulse based on the electrical input pulse, wherein the ultrasonic pulse propagates along the sensor block to a second end of the sensor block and is reflected back to the first end of the sensor block;
   (d) receiving at the electrode an electrical output pulse based on the reflected pulse;

(e) measuring a time between the applying the electrical input pulse and the receiving the electrical output pulse; and (f) calculating a temperature in the nuclear reactor.

14. The method according to claim 13, wherein the piezoelectric wafer withstands temperatures of 1000° C. or more.

15. The method according to claim 13, wherein the piezoelectric wafer comprises a pyroelectric piezoelectric material.

16. The method according to claim 15, wherein the piezoelectric wafer comprises aluminum nitride.

17. The method according to claim 15, wherein the piezoelectric wafer comprises a 5.3 mm diameter single crystal z-cut of aluminum nitride.

18. The method according to claim 15, wherein the piezoelectric wafer comprises transparent nitrogen rich aluminum nitride.

19. The method according to claim 13, wherein the piezoelectric wafer comprises a ferroelectric piezoelectric material.

* * * * *